(12) United States Patent
Leatherman et al.

(10) Patent No.: US 7,879,916 B2
(45) Date of Patent: Feb. 1, 2011

(54) HYDROLYSIS RESISTANT ORGANOMODIFIED SILYLATED IONIC SURFACTANTS

(75) Inventors: Mark D. Leatherman, Stamford, CT (US); George A. Policello, Ossining, NY (US); Wenqing Peng, Shanghai (CN); Liping Zheng, Shaghai (CN); Roland Wagner, Bonn (DE); Suresh K. Rajaraman, Newburg, NY (US); Zijun Xia, Shanghai (CN)

(73) Assignee: Momentive Performance Materials Inc., Albany, NY (US)

(*) Notice: Subject to any disclaimer, the term of this patent is extended or adjusted under 35 U.S.C. 154(b) by 104 days.

(21) Appl. No.: 11/953,167

(22) Filed: Dec. 10, 2007

(65) Prior Publication Data
US 2008/0167389 A1 Jul. 10, 2008

Related U.S. Application Data

(60) Provisional application No. 60/869,432, filed on Dec. 11, 2006.

(51) Int. Cl.
*C09K 3/00* (2006.01)
*C07F 7/08* (2006.01)
*C07F 7/04* (2006.01)

(52) U.S. Cl. .......................... 516/55; 514/63; 556/413
(58) Field of Classification Search ................ 516/115; 426/237; 96/176; 95/241
See application file for complete search history.

(56) References Cited

U.S. PATENT DOCUMENTS

| | | | |
|---|---|---|---|
| 3,159,601 A | 12/1964 | Ashby | |
| 3,220,972 A | 11/1965 | Lamoreaux | |
| 3,715,334 A | 2/1973 | Karsted | |
| 3,775,452 A | 11/1973 | Karstedt | |
| 3,814,730 A | 6/1974 | Karstedt | |
| 5,026,891 A * | 6/1991 | Colas et al. | 556/413 |
| 5,674,832 A | 10/1997 | Keys | |
| 6,046,156 A | 4/2000 | Perry et al. | |
| 6,054,547 A | 4/2000 | Perry et al. | |
| 6,060,546 A | 5/2000 | Powell et al. | |
| 6,075,111 A | 6/2000 | Perry et al. | |
| 6,077,923 A | 6/2000 | Perry et al. | |
| 6,083,901 A | 7/2000 | Perry et al. | |
| 6,153,578 A | 11/2000 | Perry et al. | |
| 6,271,295 B1 | 8/2001 | Powell et al. | |

FOREIGN PATENT DOCUMENTS

| | | |
|---|---|---|
| EP | 0367381 | 5/1990 |
| WO | 2007/127016 | 11/2007 |
| WO | 2007/133761 | 11/2007 |
| WO | 2007/133762 | 11/2007 |
| WO | 2007/139615 | 12/2007 |

OTHER PUBLICATIONS

XP001000634 Maki H et al: "Syntheses and properties of surfactants containing organometals: IV. Organo silicone" Jornal of the American Oil Chemists' Society, vol. 46, No. 12, Dec. 1969 pp. 635-638, ISSN: 0003-021X, p. 636, col. 2.

XP002477082 Chemical Abstracts; Maki, Hirohisa et al: Syntheses and properties of organometallic surface-active agents. III. Syntheses and properties of glycidyl ether derivations containing poly (dimethylsilylmethylene) groups, Publication date 1968.

XP009098950 Sawada et al: "Reactions of methyl (vinyldimethylsilyl) acetate with fluoroalkanyoyl peroxices. Synthesis of novel fluoralkylated chelating surfactants" Zairyo Gijutsu, vol. 15, No. 6, 1997, pp. 223-226.

J.L. Spier, "Homogeneous catalysis of hydrolisilation by Transition Metals," in Advances ini Organometallic Chemistry, 1979, vol. 17, pp. 407-447.

* cited by examiner

*Primary Examiner*—Ling-Siu Choi
*Assistant Examiner*—Chun-Cheng Wang
(74) *Attorney, Agent, or Firm*—Dominick G. Vicari

(57) ABSTRACT

The present invention provides for a composition comprising a silane having the formula:

$$(R^1)(R^2)(R^3)Si-R^4-Si(R^5)(R^6)(R^7)$$

wherein
$R^1$, $R^2$, $R^3$, $R^5$, and $R^6$ are each independently selected from the group consisting of 1 to 6 monovalent hydrocarbon radicals, aryl, and a hydrocarbon group of 7 to 10 carbons containing an aryl group;
$R^4$ is a hydrocarbon group of 1 to 3 carbons;
$R^7$ comprises an anionic, cationic or zwitterionic substituent. The silanes of the present invention exhibit resistance to hydrolysis over a wide pH range.

6 Claims, No Drawings

HYDROLYSIS RESISTANT ORGANOMODIFIED SILYLATED IONIC SURFACTANTS

CROSS-REFERENCE TO RELATED APPLICATIONS

This application claims priority to U.S. provisional patent application Ser. No. 60/869,432 filed Dec. 11, 2006.

FIELD OF THE INVENTION

The present invention relates to silane compositions that exhibit resistance to hydrolysis over a wide pH range. More particularly the present invention relates to such hydrolysis-resistant silanes having a resistance to hydrolysis between a pH of about 2 to a pH of about 12.

BACKGROUND OF THE INVENTION

The topical application of liquid compositions to the surfaces of both animate and inanimate objects to effect a desired change involve the processes of controlling wetting, spreading, foaming, detergency, and the like. When used in aqueous solutions to improve the delivery of active ingredients to the surface being treated, trisiloxane-type compounds have been found to be useful in enabling the control of these processes to achieve the desired effect. However, the trisiloxane compounds may only be used in a narrow pH range, ranging from a slightly acidic pH of 6 to a very mildly basic pH of 7.5. Outside this narrow pH range, the trisiloxane compounds are not stable to hydrolysis, undergoing rapid decomposition.

SUMMARY OF THE INVENTION

The present invention provides for an silane compound or compositions thereof useful as a surfactant having the general formula:

$$(R^1)(R^2)(R^3)Si-R^4-Si(R^5)(R^6)(R^7)$$

wherein $R^1$, $R^2$, $R^3$, $R^5$, and $R^6$ are each independently selected from the group consisting of 1 to 6 monovalent hydrocarbon radicals, aryl, and a hydrocarbon group of 7 to 10 carbons containing an aryl group;

$R^4$ is a hydrocarbon group of 1 to 3 carbons.

$R^7$ is $R^8$-$R^A$, $R^9$-$R^C$, and $R^{10}$-$R^Z$;

$R^8$ is selected from the group consisting of $R^{11}(O)_t(R^{12})_u(O)_v-$,

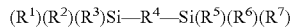

$R^{13}-CHCH_2CH(OH)CH(O-)CH_2CH_2$; and

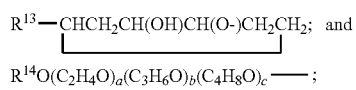

$R^{14}O(C_2H_4O)_a(C_3H_6O)_b(C_4H_8O)_c-$;

where $R^{11}$ and $R^{12}$ are each independently selected from the group consisting of a divalent hydrocarbon group of 1 to 4 carbon atoms, that may each be optionally substituted with one or more OH radicals; $R^{13}$ is a divalent hydrocarbon group of 2 to 4 carbon atoms; $R^{14}$ is a divalent hydrocarbon group of 1 to 6 carbons, that may each be optionally branched; subscripts t, u and v are zero or 1. The subscripts a, b and c are zero or positive and satisfy the following relationships:

$1 \leq a+b+c \leq 10$ with $a \geq 1$.

$R^A$ is a monovalent radical selected from the group consisting of $-SO_3M^K$, $-C(=O)CH_2CH(R^{15})COO-M^K$; $-PO_3HM^K$; $-COOM^K$; where $R^{15}$ is H or $-SO_3M^K$; $M^K$ is a cation selected from the group consisting of Na$^+$, K$^+$, Ca$^{2+}$, NH$_4^+$, Li$^+$, and monovalent ammonium ions derived from mono-, di- and trialkylamines of 2 to 4 carbons or mono-, di- and trialkanolamines of 2 to 4 carbons.

$R^9$ is a monovalent radical selected from the group consisting of $R^{16}(O)_w(R^{17})_x-$ and $R^{18}O(C_2H_4O)_d(C_3H_6O)_e(C_4H_8O)_fCH_2CH(OH)CH_2-$;

where $R^{16}$ and $R^{17}$ are each independently selected from the group consisting of a divalent hydrocarbon group of 1 to 4 carbon atoms, that may each be optionally substituted with one or more OH radicals; $R^{18}$ is a divalent hydrocarbon group of 2 to 4 carbon atoms; subscripts w and x are zero or 1. The subscripts d, e and f are zero or positive and satisfy the following relationships:

$1 \leq d+e+f \leq 10$ with $d \geq 1$.

$R^C$ is selected from $N(R^{19})(R^{20})$,

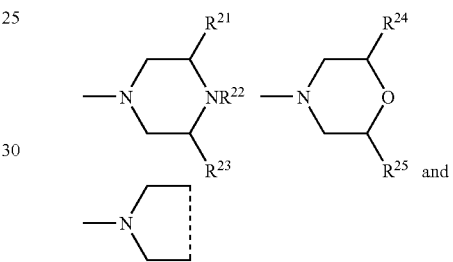

where $R^{19}$ and $R^{20}$ are independently selected from the group consisting of H, a branched or linear monovalent hydrocarbon radical of 1 to 4 carbons, $R^{26}N(R^{29})(R^{30})$, and $-R^{27}O(C_2H_4O)_g(C_3H_6O)_h(C_4H_8O)_iR^{28}$. The subscripts g, h and are zero or positive and satisfy the following relationships:

$1 \leq g+h+i \leq 10$ with $g \geq 1$.

$R^{21}$, $R^{23}$, $R^{24}$, $R^{25}$ are each independently selected from the groups consisting of H, a branched or linear monovalent hydrocarbon radical of 1 to 4 carbons.

$R^{22}$ is a monovalent radical selected from the group consisting of H, a branched or linear monovalent hydrocarbon radical of 1 to 4 carbons, or $-R^{31}O(C_2H_4O)_j(C_3H_6O)_k(C_4H_8O)_lR^{32}$; the subscripts j, k and l are zero or positive and satisfy the following relationships:

$1 \leq j+k+1 \leq 10$ with $j \geq 1$.

$R^{26}$ is a divalent hydrocarbon radical of 1 to 6 carbons, optionally substituted with a heterocyclic group containing nitrogen, sulfur, oxygen or combinations thereof or $R^{33}O(C_2H_4O)_m(C_3H_6O)_n(C_4H_8O)_oR^{34}$; the subscripts m, n and o are zero or positive and satisfy the following relationships:

$1 \leq m+n+o \leq 10$ with $m \geq 1$.

$R^{29}$ and $R^{30}$ are independently selected from the group consisting of H or a branched or linear monovalent hydrocarbon radical of 1 to 4 carbons.

$R^{27}$, $R^{31}$ and $R^{33}$ are independently selected from the group consisting of a divalent hydrocarbon group of 2 to 4 carbon atoms.

$R^{28}$ is a monovalent radical selected from the group consisting of H, a monovalent hydrocarbon radical of 1 to 6 carbons and $N(R^{40})(R^{41})$.

$R^{32}$ and $R^{34}$ are independently selected from the group consisting of H, a branched or linear monovalent hydrocarbon radical of 1 to 4 carbons, and $R^{37}N(R^{38})(R^{39})$; where $R^{37}$ is a divalent hydrocarbon radical of 1 to 6 carbons. $R^{35}$, $R^{36}$, $R^{38}$ and $R^{39}$ are independently selected from the group consisting of H and branched or linear monovalent hydrocarbon radicals of 1 to 4 carbons.

$R^{10}$ is a monovalent radical selected from the group consisting of $R^{40}(O)_y(R^{41})_z$— and $R^{42}O(C_2H_4O)_p(C_3H_6O)_q(C_4H_8O)_rCH_2CH(OH)CH_2$—; where $R^{40}$ and $R^{41}$ are each independently selected from the group consisting of a divalent hydrocarbon group of 1 to 4 carbon atoms, that may each be optionally substituted with one or more OH radicals; $R^{42}$ is a divalent hydrocarbon group of 2 to 4 carbon atoms; subscripts y and z are zero or 1. The subscripts p, q and r are zero or positive and satisfy the following relationships:

$$1 \leq p+q+r \leq 10 \text{ with } p \geq 1.$$

$R^Z$ is —N—$(R^{43})(R^{44})_\alpha R^{45}SO_3(M^K)_\beta$, —N—$(R^{46})(R^{47})_\gamma R^{48}COO(M^K)_\delta$, —N$^+$—$(R^{49})(R^{50})R^{51}OP$ (=O)(A)(B) or, (—C(=O)N$(R^{52})R^{53}$N—$(R^{54})(R^{55}))^+$—$(R^{56}OP$(=O)(A)(B))(X$^-$)$_\epsilon$;

where $R^{43}$, $R^{44}$, $R^{46}$, $R^{47}$, $R^{49}$, $R^{50}$, $R^{52}$, $R^{54}$ and $R^{55}$ are independently selected from the group consisting of H, a branched or linear monovalent hydrocarbon radical of 1 to 4 carbons, and an alkanolamine group of 2 to 4 carbons. $R^{45}$ is a divalent group of 3 to 4 carbons; subscripts α, β, γ and δ are zero or 1 subject to the following relationships: α+β is selected from the group consisting of 1 and γ+δ is selected from the group consisting of 1.

$R^{48}$ and $R^{51}$ are independently a divalent group of 1 to 4 carbons.

$R^{53}$ and $R^{56}$ are each independently a divalent group of 2 to 4 carbons.

A and B are selected from O$^-$ and OM$^K$; X is an anion selected from the group of anions consisting of Cl, Br, and I; the subscript ε is 0, 1 or 2.

Particularly useful embodiments of the present invention are exemplified by the following choices for species: $R^1$, $R^2$, $R^3$, $R^5$ and $R^6$ are methyl; $R^4$ is —CH$_2$CH$_2$— or —CH$_2$CH$_2$CH$_2$—; $R^{11}$ is —CH$_2$CH$_2$CH$_2$—; $R^{12}$ is —CH$_2$CH(OH)CH$_2$—; $R^{13}$ is —CH$_2$CH$_2$—; $R^{14}$ is —CH$_2$CH$_2$CH$_2$—, —CH(CH$_3$)CH$_2$CH$_2$—, or —CH$_2$CH(CH$_3$)CH$_2$—; a, b and c=0; t=1, u=1, v=0; $R^{15}$=H; $M^K$ is Na$^+$, K$^+$ or NH$_4^+$; $R^{16}$ is —CH$_2$CH$_2$CH$_2$—; $R^{17}$ is —CH$_2$CH(OH)CH$_2$—; $R^{18}$ is —CH$_2$CH$_2$CH$_2$—; d, e, and f=0; w=1, x=1; $R^{19}$ and $R^{20}$ are H, methyl, ethyl, propyl, isopropyl or —R$^{27}$O(C$_2$H$_4$O)$_g$(C$_3$H$_6$O)$_h$(C$_4$H$_8$O)$_i$R$^{28}$; $R^{27}$ is —CH$_2$CH$_2$CH$_2$—; g is 1-5, h and i=0; $R^{27}$ is H or methyl; $R^{21}$ and $R^{23}$ are H; $R^{22}$=H, methyl or —R$^{31}$O(C$_2$H$_4$O)$_j$(C$_3$H$_6$O)$_k$(C$_4$H$_8$O)$_l$R$^{32}$; $R^{31}$ is —CH$_2$CH$_2$CH$_2$—; j is 1-5, k and l=0; $R^{32}$ is H or methyl; $R^{24}$ and $R^{25}$ are H; $R^{40}$ is —CH$_2$CH$_2$CH$_2$—; $R^{41}$ is —CH$_2$CH(CH$_3$)CH$_2$—; y and z=1; $R^{42}$ is —CH$_2$CH$_2$CH$_2$—; p is 1-5, q and r=0; $R^{43}$ and $R^{44}$ are H or methyl; $R^{45}$ is —CH$_2$CH$_2$CH$_2$— or —CH$_2$CH$_2$CH$_2$CH$_2$—; $M^K$=Na$^+$, K$^+$ or NH$_4^+$;

$R^{46}$ and $R^{47}$ are H or methyl; $R^{48}$ is —CH$_2$CH$_2$CH$_2$— or —CH$_2$CH$_2$CH$_2$CH$_2$—;

$R^{49}$ and $R^{50}$ are H or methyl; and $R^{52}$, $R^{54}$ and $R^{55}$ are H or methyl.

DETAILED DESCRIPTION OF THE INVENTION

As used herein, integer values of stoichiometric subscripts refer to molecular species and non-integer values of stoichiometric subscripts refer to a mixture of molecular species on a molecular weight average basis, a number average basis or a mole fraction basis.

The present invention provides for an silane compound or compositions thereof useful as a surfactant having the general formula:

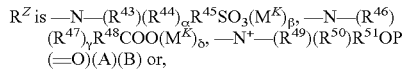

wherein $R^1$, $R^2$, $R^3$, $R^5$, and $R^6$ are each independently selected from the group consisting of 1 to 6 monovalent hydrocarbon radicals, aryl, and a hydrocarbon group of 7 to 10 carbons containing an aryl group;

$R^4$ is a hydrocarbon group of 1 to 3 carbons.

$R^7$ is $R^8$- $R^A$, $R^9$- $R^C$, and $R^{10}$- $R^Z$;

$R^8$ is selected from the group consisting of $R^{11}(O)_t(R^{12})_u(O)_v$—,

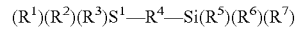

$R^{13}$—CHCH$_2$CH(OH)CH(O-)CH$_2$CH$_2$; and $R^{14}$O(C$_2$H$_4$O)$_a$(C$_3$H$_6$O)$_b$(C$_4$H$_8$O)$_c$——;

where $R^{11}$ and $R^{12}$ are each independently selected from the group consisting of a divalent hydrocarbon group of 1 to 4 carbon atoms, that may each be optionally substituted with one or more OH radicals; $R^{13}$ is a divalent hydrocarbon group of 2 to 4 carbon atoms; $R^{14}$ is a divalent hydrocarbon group of 1 to 6 carbons, that may each be optionally branched; subscripts t, u and v are zero or 1. The subscripts a, b and c are zero or positive and satisfy the following relationships:

$$1 \leq a+b+c \leq 10 \text{ with } a \geq 1.$$

$R^A$ is a monovalent radical selected from the group consisting of —SO$_3$M$^K$, —C(=O)CH$_2$CH(R$^{15}$)COO$^-$M$^K$; —PO$_3$HM$^K$; —COOM$^K$; where $R^{15}$ is H or —SO$_3$M$^K$; $M^K$ is a cation selected from the group consisting of Na$^+$, K$^+$, Ca$^{2+}$, NH$_4^+$, Li$^+$, and monovalent ammonium ions derived from mono-, di- and trialkylamines of 2 to 4 carbons or mono-, di- and trialkanolamines of 2 to 4 carbons.

$R^9$ is a monovalent radical selected from the group consisting of $R^{16}(O)_w(R^{17})_x$— and $R^{18}O(C_2H_4O)_d(C_3H_6O)_e(C_4H_8O)_f$CH$_2$CH(OH)CH$_2$—;

where $R^{16}$ and $R^{17}$ are each independently selected from the group consisting of a divalent hydrocarbon group of 1 to 4 carbon atoms, that may each be optionally substituted with one or more OH radicals; $R^{18}$ is a divalent hydrocarbon group of 2 to 4 carbon atoms; subscripts w and x are zero or 1. The subscripts d, e and f are zero or positive and satisfy the following relationships:

$$1 \leq d+e+f \leq 10 \text{ with } d \geq 1.$$

$R^C$ is selected from $N(R^{19})(R^{20})$,

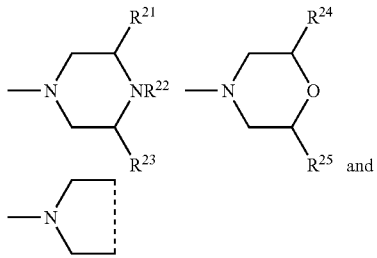

where $R^{19}$ and $R^{20}$ are independently selected from the group consisting of H, a branched or linear monovalent hydrocarbon radical of 1 to 4 carbons, $R^{26}N(R^{29})(R^{30})$, and $-R^{27}O(C_2H_4O)_g(C_3H_6O)_h(C_4H_8O)_iR^{28}$. The subscripts g, h and are zero or positive and satisfy the following relationships:

$$1 \leq g+h+i \leq 10 \text{ with } g \geq 1.$$

$R^{21}$, $R^{23}$, $R^{24}$, $R^{25}$ are each independently selected from the groups consisting of H, a branched or linear monovalent hydrocarbon radical of 1 to 4 carbons.

$R^{22}$ is a monovalent radical selected from the group consisting of H, a branched or linear monovalent hydrocarbon radical of 1 to 4 carbons, or $-R^{31}O(C_2H_4O)_j(C_3H_6O)_k(C_4H_8O)_lR^{32}$; the subscripts j, k and l are zero or positive and satisfy the following relationships:

$$1 \leq j+k+l \leq 10 \text{ with } j \geq 1.$$

$R^{26}$ is a divalent hydrocarbon radical of 1 to 6 carbons, optionally substituted with a heterocyclic group containing nitrogen, sulfur, oxygen or combinations thereof or $R^{33}O(C_2H_4O)_m(C_3H_6O)_n(C_4H_8O)_oR^{34}$; the subscripts m, n and o are zero or positive and satisfy the following relationships:

$$1 \leq m+n+o \leq 10 \text{ with } m \geq 1.$$

$R^{29}$ and $R^{30}$ are independently selected from the group consisting of H or a branched or linear monovalent hydrocarbon radical of 1 to 4 carbons.

$R^{27}$, $R^{31}$ and $R^{33}$ are independently selected from the group consisting of a divalent hydrocarbon group of 2 to 4 carbon atoms.

$R^{28}$ is a monovalent radical selected from the group consisting of H, a monovalent hydrocarbon radical of 1 to 6 carbons and $N(R^{40})(R^{41})$.

$R^{32}$ and $R^{34}$ are independently selected from the group consisting of H, a branched or linear monovalent hydrocarbon radical of 1 to 4 carbons, and $R^{37}N(R^{38})(R^{39})$; where $R^{37}$ is a divalent hydrocarbon radical of 1 to 6 carbons. $R^{35}$, $R^{36}$, $R^{38}$ and $R^{39}$ are independently selected from the group consisting of H and branched or linear monovalent hydrocarbon radicals of 1 to 4 carbons.

$R^{10}$ is a monovalent radical selected from the group consisting of $R^{40}(O)_y(R^{41})_z-$ and $R^{42}O(C_2H_4O)_p(C_3H_6O)_q(C_4H_8O)_r CH_2CH(OH)CH_2-$;

where $R^{40}$ and $R^{41}$ are each independently selected from the group consisting of a divalent hydrocarbon group of 1 to 4 carbon atoms, that may each be optionally substituted with one or more OH radicals; $R^{42}$ is a divalent hydrocarbon group of 2 to 4 carbon atoms; subscripts y and z are zero or 1. The subscripts p, q and r are zero or positive and satisfy the following relationships:

$$1 \leq p+q+r \leq 10 \text{ with } p \geq 1.$$

$R^Z$ is $-N-(R^{43})(R^{44})_\alpha R^{45}SO_3(M^K)_\beta$, $-N-(R^{46})(R^{47})_\gamma R^{48}COO(M^K)_\delta$, $-N^+-(R^{49})(R^{50})R^{51}OP(=O)(A)(B)$ or, $(-C(=O)N(R^{52})R^{53}N-(R^{54})(R^{55}))^+-(R^{56}OP(=O)(A)(B))(X^-)_\epsilon$;

where $R^{43}$, $R^{44}$, $R^{46}$, $R^{47}$, $R^{49}$, $R^{50}$, $R^{52}$, $R^{54}$ and $R^{55}$ are independently selected from the group consisting of H, a branched or linear monovalent hydrocarbon radical of 1 to 4 carbons, and an alkanolamine group of 2 to 4 carbons. $R^{45}$ is a divalent group of 3 to 4 carbons; subscripts $\alpha$, $\beta$, $\gamma$ and $\delta$ are zero or 1 subject to the following relationships: $\alpha+\beta$ is selected from the group consisting of 1 and $\gamma+\delta$ is selected from the group consisting of 1.

$R^{43}$ and $R^{56}$ are independently a divalent group of 1 to 4 carbons.

$R^{53}$ and $R^{56}$ are each independently a divalent group of 2 to 4 carbons.

A and B are selected from O⁻ and OM$^K$; X is an anion selected from the group of anions consisting of Cl, Br, and I; the subscript is 0, 1 or 2.

Particularly useful embodiments of the present invention are exemplified by the following choices for species: $R^1$, $R^2$, $R^3$, $R^5$ and $R^6$ are methyl; $R^4$ is $-CH_2CH_2-$ or $-CH_2CH_2CH_2-$; $R^{11}$ is $-CH_2CH_2CH_2-$; $R^{12}$ is $-CH_2CH(OH)CH_2-$; $R^{13}$ is $-CH_2CH_2-$; $R^{14}$ is $-CH_2CH_2CH_2-$, $-CH(CH_3)CH_2CH_2-$, or $-CH_2CH(CH_3)CH_2-$; a, b and c=0; t=1, u=1, v=0; $R^{15}$=H; MK is Na⁺, K⁺ or NH$_4^+$; $R^{16}$ is $-CH_2CH_2CH_2-$; $R^{17}$ is $-CH_2CH(OH)CH_2-$; $R^{18}$ is $-CH_2CH_2CH_2-$; d, e, and f=0; w=1, x=1; $R^{19}$ and $R^{20}$ are H, methyl, ethyl, propyl, isopropyl or $-R^{27}O(C_2H_4O)_g(C_3H_6O)_h(C_4H_8O)_iR^{28}$; $R^{27}$ is $-CH_2CH_2CH_2-$; g is 1-5, h and i=0; $R^{27}$ is H or methyl; $R^{21}$ and $R^{23}$ are H; $R^{22}$=H, methyl or $-R^{31}O(C_2H_4O)_j(C_3H_6O)_k(C_4H_8O)_lR^{32}$; $R^{31}$ is $-CH_2CH_2CH_2-$; j is 1-5, k and l=0; $R^{32}$ is H or methyl; $R^{24}$ and $R^{25}$ are H; $R^{40}$ is $-CH_2CH_2CH_2-$; $R^{41}$ is $-CH_2CH(CH_3)CH_2-$;

y and z=1; $R^{42}$ is $-CH_2CH_2CH_2-$; p is 1-5, q and r=0; $R^{43}$ and $R^{44}$ are H or methyl; $R^{45}$ is $-CH_2CH_2CH_2-$ or $-CH_2CH_2CH_2CH_2-$; $M^K$=Na⁺, K⁺ or NH$_4^+$;

$R^{46}$ and $R^{47}$ are H or methyl; $R^{48}$ is $-CH_2CH_2CH_2-$ or $-CH_2CH_2CH_2CH_2-$;

$R^{49}$ and $R^{50}$ are H or methyl; and $R^{52}$, $R^{54}$ and $R^{55}$ are H or methyl.

One method of producing the composition of the present invention is to react a molecule of the following formula:

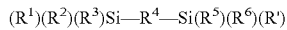

$(R^1)(R^2)(R^3)Si-R^4-Si(R^5)(R^6)(R')$ where R' is H, wherein the definitions and relationships are later defined and consistent with those defined above, under hydrosilylation conditions, with an olefinically modified epoxy-containing moiety, such as allyl glycidyl ether or vinyl cyclohexene oxide, which are incorporated here as examples, and not set forth to limit other possible olefinically modified epoxy components, followed by subsequent reaction with an amine-containing group.

Epoxy-modified carbosilanes are straightforwardly prepared through the use of a hydrosilylation reaction to graft the olefinically modified (i.e. vinyl, allyl or methallyl) epoxy group onto the hydride (SiH) intermediate of the carbosilane of the present invention.

Precious metal catalysts suitable for making epoxy-substituted silanes are also well known in the art and comprise complexes of rhodium, ruthenium, palladium, osmium, iridium, and/or platinum. Many types of platinum catalysts for this SiH-olefin addition reaction are known and such platinum catalysts may be used to generate the compositions of the present invention. The platinum compound can be selected from those having the formula ($PtC_2Olefin$) and $H(PtCl_3Olefin)$ as described in U.S. Pat. No. 3,159,601, hereby incorporated by reference. A further platinum containing material can be a complex of chloroplatinic acid with up to 2 moles per gram of platinum of a member selected from the class consisting of alcohols, ethers, aldehydes and mixtures thereof as described in U.S. Pat. No. 3,220,972, hereby incorporated by reference. Yet another group of platinum containing materials useful in this present invention is described in U.S. Pat. Nos. 3,715,334; 3,775,452 and 3,814,730 (Karstedt). Additional background concerning the art may be found in J. L. Spier, "Homogeneous Catalysis of Hydrosilation by Transition Metals", in Advances in Organometallic Chemistry, volume 17, pages 407 through 447, F. G. A. Stone and R. West editors, published by Academic Press (New York, 1979). Those skilled in the art can easily determine an effective amount of platinum catalyst. Generally an effective amount ranges from about 0.1 to 50 parts per million of the total silane composition.

Uses for the Compositions of the Present Invention:

A. Pesticide—Agriculture, Horticulture, Turf, Ornamental and Forestry

Many pesticide applications require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, enhance spreading to improve spray coverage, or to provide penetration of the herbicide into the plant cuticle. These adjuvants are provided either as a tank-side additive or used as a component in pesticide formulations.

Typical uses for pesticides include agricultural, horticultural, turf, ornamental, home and garden, veterinary and forestry applications.

The pesticidal compositions of the present invention also include at least one pesticide, where the silane of the present invention is present at an amount sufficient to deliver between 0.005% and 2% to the final use concentration, either as a concentrate or diluted in a tank mix. Optionally the pesticidal composition may include excipients, cosurfactants, solvents, foam control agents, deposition aids, drift retardants, biologicals, micronutrients, fertilizers and the like. The term pesticide means any compound used to destroy pests, e.g., rodenticides, insecticides, miticides, fungicides, and herbicides. Illustrative examples of pesticides that can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are, but not limited to, herbicides and growth regulators, such as phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

Fungicide compositions that can be used with the present invention include, but are not limited to, aldimorph, tridemorph, dodemorph, dimethomorph; flusilazol, azaconazole, cyproconazole, epoxiconazole, furconazole, propiconazole, tebuconazole and the like; imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, maneb, mancozeb, dodicin, dodine, and metalaxyl.

Insecticide, larvacide, miticide and ovacide compounds that can be used with the composition of the present invention, but not limited to, *Bacillus thuringiensis*, spinosad, abamectin, doramectin, lepimectin, pyrethrins, carbaryl, primicarb, aldicarb, methomyl, amitraz, boric acid, chlordimeform, novaluron, bistrifluoron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrin and the like.

The pesticide may be a liquid or a solid. If a solid, it is preferable that it is soluble in a solvent, or the silane of the present invention, prior to application, and the silane may act as a solvent, or surfactant for such solubility or additional surfactants may perform this function.

Agricultural Excipients:

Buffers, preservatives and other standard excipients known in the art also may be included in the composition.

Solvents may also be included in compositions of the present invention. These solvents are in a liquid state at room temperature. Examples include water, alcohols, aromatic solvents, oils (i.e. mineral oil, vegetable oil, silicone oil, and so forth), lower alkyl esters of vegetable oils, fatty acids, ketones, glycols, polyethylene glycols, diols, paraffinics, and so forth. Particular solvents would be 2,2,4-trimethyl, 1-3-pentane diol and alkoxylated (especially ethoxylated) versions thereof as illustrated in U.S. Pat. No. 5,674,832 herein incorporated by reference, or N-methyl-pyrrilidone.

Cosurfactants:

Moreover, other cosurfactants, which have short chain hydrophobes that do not interfere with superspreading as described in U.S. Pat. No. 5,558,806 are herein included by reference.

The cosurfactants useful herein include nonionic, cationic, anionic, amphoteric, zwitterionic, polymeric surfactants, or any mixture thereof.

Surfactants are typically hydrocarbon based, silicone based or fluorocarbon based.

Useful surfactants include alkoxylates, especially ethoxylates, containing block copolymers including copolymers of ethylene oxide, propylene oxide, butylene oxide, and mixtures thereof; alkylarylalkoxylates, especially ethoxylates or propoxylates and their derivatives including alkyl phenol ethoxylate; arylarylalkoxylates, especially ethoxylates or propoxylates, and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines; and so forth.

Specific examples include alkyl acetylenic diols (SURFO-NYL-Air Products), pyrrilodone based surfactants (e.g., SURFADONE-LP 100-ISP), 2-ethyl hexyl sulfate, isodecyl alcohol ethoxylates (e.g., RHODASURF DA 530-Rhodia), ethylene diamine alkoxylates (TETRONICS-BASF), and ethylene oxide/propylene oxide copolymers (PLURONICS-BASF) and Gemini type surfactants (Rhodia).

Preferred surfactants include ethylene oxide/propylene oxide copolymers (EO/PO); amine ethoxylates; alkyl polyglycosides; oxo-tridecyl alcohol ethoxylates, and so forth.

In a preferred embodiment, the agrochemical composition of the present invention further comprises one or more agrochemical ingredients. Suitable agrochemical ingredients include, but not limited to, herbicides, insecticides, growth regulators, fungicides, miticides, acaricides, fertilizers, biologicals, plant nutritionals, micronutrients, biocides, paraffinic mineral oil, methylated seed oils (i.e. methylsoyate or methylcanolate), vegetable oils (such as soybean oil and canola oil), water conditioning agents such as Choice® (Loveland Industries, Greeley, Colo.) and Quest (Helena Chemical, Collierville, Tenn.), modified clays such as Surround® (Englehard Corp.,), foam control agents, surfactants, wetting agents, dispersants, emulsifiers, deposition aids, anti-drift components, and water.

Suitable agrochemical compositions are made by combining, in a manner known in the art, such as by mixing, one or more of the above components with the silane of the present invention, either as a tank-mix, or as an "in-can" formulation. The term "tank-mix" means the addition of at least one agrochemical to a spray medium, such as water or oil, at the point of use. The term "in-can" refers to a formulation or concentrate containing at least one agrochemical component. The "in-can" formulation may then diluted to use concentration at the point of use, typically in a tank-mix, or it may be used undiluted.

The silane compositions of the present invention may be utilized in agricultural emulsions. The different types of emulsions are explained hereinafter as varieties of personal care compositions.

B. Coatings

Typically, coatings formulations will require a wetting agent or surfactant for the purpose of emulsification, compatibilization of components, leveling, flow and reduction of surface defects. Additionally, these additives may provide improvements in the cured or dry film, such as improved abrasion resistance, antiblocking, hydrophilic and hydrophobic properties. Coating formulations may exist as solvent-borne coatings, water-borne coatings and powder coatings.

The coatings components may be employed as architecture coatings, OEM product coatings such as automotive coatings and coil coatings, special purpose coatings such as industrial maintenance coatings and marine coatings. Typical synthetic resin types for coatings substrates include polyesters, polyurethanes, polycarbonates, acrylics and epoxies.

C. Personal Care

In a preferred embodiment, the silane of the present invention comprises, per 100 parts by weight ("pbw") of the personal care composition, from 0.1 to 99 pbw, more preferably from 0.5 pbw to 30 pbw and still more preferably from 1 to 15 pbw of the silane and from 1 pbw to 99.9 pbw, more preferably from 70 pbw to 99.5 pbw, and still more preferably from 85 pbw to 99 pbw of the personal care composition.

The silane compositions of the present invention may be utilized in personal care emulsions, such as lotions, and creams. As is generally known, emulsions comprise at least two immiscible phases, one of which is continuous and the other discontinuous. Further, emulsions may be liquids with varying viscosities or solids. Additionally the particle size of the emulsions may render them microemulsions, and when the particle sizes are sufficiently small, microemulsions may be transparent. Further, it is also possible to prepare emulsions of emulsions and these are generally known as multiple emulsions. These emulsions may be:

1) aqueous emulsions where the discontinuous phase comprises water and the continuous phase comprises the silane of the present invention;

2) aqueous emulsions where the discontinuous phase comprises the silane of the present invention and the continuous phase comprises water;

3) non-aqueous emulsions where the discontinuous phase comprises a non-aqueous hydroxylic solvent and the continuous phase comprises the silane of the present invention; and 4) non-aqueous emulsions where the discontinuous phase comprises the silane of the present invention and the continuous phase comprises a non-aqueous hydroxylic organic solvent.

Non-aqueous emulsions comprising a silicone phase are described in U.S. Pat. Nos. 6,060,546 and 6,271,295, the disclosures of which are herewith and hereby specifically incorporated by reference.

As used herein, the term "non-aqueous hydroxylic organic compound" means hydroxyl-containing organic compounds exemplified by alcohols, glycols, polyhydric alcohols and polymeric glycols, and mixtures thereof that are liquid at room temperature, e.g. about 25° C., and about one atmosphere pressure. The non-aqueous organic hydroxylic solvents are selected from the group consisting of hydroxyl-containing organic compounds comprising alcohols, glycols, polyhydric alcohols and polymeric glycols, and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, isopropyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a cream or lotion with improved deposition properties and good feel characteristics. It is capable of being blended into formulations for hair care, skin care, antiperspirants, sunscreens, cosmetics, color cosmetics, insect repellants, vitamin and hormone carriers, fragrance carriers and the like.

The personal care applications where the silane of the present invention and the silicone compositions derived therefrom of the present invention may be employed include, but are not limited to, deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a preferred embodiment, the personal care composition of the present invention further comprises one or more personal care ingredients.

Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with the silane. Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions.

In one useful embodiment, an antiperspirant composition comprises the silane of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex gly.

In another useful embodiment, a skin care composition comprises the silane, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylm ethane, p-aminobenzoic acid and octyl dimethyl-p-aminobenzoic acid.

In another useful embodiment, a color cosmetic composition, such as, for example, a lipstick, a makeup or a mascara composition comprises the silane, and a coloring agent, such as a pigment, a water soluble dye or a liposoluble dye.

In another useful embodiment, the compositions of the present invention are utilized in conjunction with fragrant materials. These fragrant materials may be fragrant compounds, encapsulated fragrant compounds, or fragrance releasing compounds that either the neat compounds or are encapsulated. Particularly compatible with the compositions of the present invention are the fragrance-releasing silicon-containing compounds as disclosed in U.S. Pat. Nos. 6,046,156; 6,054,547; 6,075,111; 6,077,923; 6,083,901; and 6,153,578; all of which are herein and herewith specifically incorporated by reference.

The uses of the compositions of the present invention are not restricted to personal care compositions, other products such as waxes, polishes and textiles treated with the compositions of the present invention are also contemplated.

D. Home Care

Compositions of the present silane invention are useful in home care applications, including laundry detergent and fabric softener, dishwashing liquids, wood and furniture polish, floor polish, tub and tile cleaners, toilet bowl cleaners, hard surface cleaners, window cleaners, antifog agents, drain cleaners, auto-dishwashing detergents and sheeting agents, carpet cleaners, prewash spotters, rust cleaners and scale removers.

E. Oil and Gas

Compositions of the present silane invention are useful in oil and gas applications, including demulsification.

F. Water Treatment

Compositions comprising silane invention are useful for applications involving commercial and industrial open recirculating cooling water towers, closed cooling water systems, cooling water conduits, heat exchangers, condensers, once-through cooling systems, Pasteurizers, air washers, heat exchange systems, air conditioning/humidifiers/dehumidifiers, hydrostatic cookers, safety and/or fire water protection storage systems, water scrubbers, disposal wells, influent water systems, including filtration and clarifiers, wastewater treatment, wastewater treatment tanks, conduits, filtration beds, digesters, clarifiers, holding ponds, settling lagoons, canals, odor control, ion exchange resin beds, membrane filtration, reverse osmosis, micro- and ultra-filtration, assisting in the removal of biofilms in cooling tower applications, heat exchangers and process water systems, and the like.

G. Pulp and Paper

Compositions of the present silane invention are useful in pulp and paper applications, such as paperboard defoamers, and wetting agents for the pulping process.

The compositions of the present invention exhibit an enhanced resistance to hydrolysis outside a pH range ranging from 6 to 7.5. Enhanced resistance to hydrolysis can be demonstrated by a variety of tests but as used herein enhanced resistance to hydrolysis means 50 mole percent or more of the hydrolysis-resistant composition of the present invention remains unchanged or unreacted after a period of a twenty-four exposure to aqueous acidic conditions where the solution has a pH lower than 6 or after a period of a twenty-four hour exposure to aqueous basic conditions where the solution has a pH greater than 7.5. Under acidic conditions the compositions of the present invention show a survival of 50 mole percent of the original concentration or greater at a pH of 5 or less for a period of time in excess of 48 hours; specifically the compositions of the present invention show a survival of 50 mole percent or greater at a pH of 5 or less for a period of time in excess of 2 weeks; more specifically the compositions of the present invention show a survival of 50 mole percent or greater at a pH of 5 or less for a period of time in excess of 1 month; and most specifically the compositions of the present invention show a survival of 50 mole percent or greater at a pH of 5 or less for a period of time in excess of 6 months. Under basic conditions the compositions of the present invention show a survival of 50 mole percent or greater at a pH of 8 or more for a period of time in excess of 2 weeks; specifically the compositions of the present invention show a survival of 50 mole percent or greater at a pH of 8 or more for a period of time in excess of 4 weeks; more specifically the compositions of the present invention show a survival of 50 mole percent or greater at a pH of 8 or more for a period of time in excess of 6 months; and most specifically the compositions of the present invention show a survival of 50 mole percent or greater at a pH of 8 or more for a period of time in excess of 1 year.

EXPERIMENTAL

The hydride intermediates for the silane compositions of the present invention, as well as comparative compositions were prepared as described in the following examples.

Preparation Example 1

N,N-dimethyl aminopropyl pentamethyl carbodisilane (Figure 1). 16.0 g pentamethyl carbodisilane and 20 μL platinum 1,3-divinyl-1,1,3,3-tetramethyldiloxane complex (0.3 wt % solution in xylene) were charged into 100 mL Schlenk flask. The mixture was heated to 90° C. and 9.35 g N,N-dimethyl allyl amine was added dropwise in 20 min. After addition, the reaction temperature was maintained at 90° C. for 3 hrs and the reaction was monitored by $^1$HNMR. After removing solvent under vacuum, the mixture was distilled under reduced pressure, and 17.0 g colorless oil was collected at 109-111° C./15 mmHg.

Figure 1. Reaction Sequence for Preparation of Amino Silane Intermediate 1.

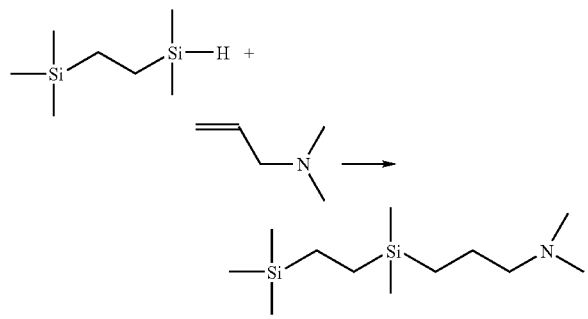

Preparation Example 2

3-({3-[Dimethyl-(2-trimethylsilanyl-ethyl)-silanyl]-propyl}-dimethyl-amino)-propane-1-sulfonate (Figure 2). 2.0 g N,N-dimethyl aminopropyl pentamethyl carbodisilane 1 and 1.10 g1,3-propanesultone were dissolved in 15 ml dry THF. The mixture was heated to reflux overnight. After removing solvent, 3.03 g white solid was obtained.

Figure 2. Reaction Sequence for Preparation of Silane 2.

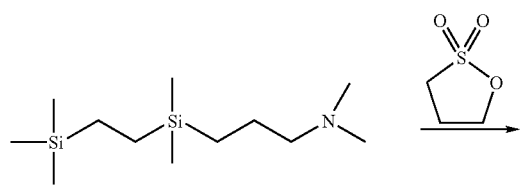

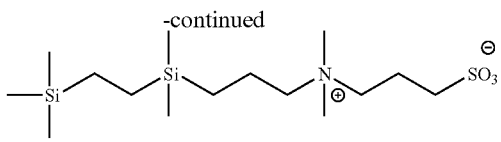

Preparation Example 3

4-([3-[Dimethyl-(2-trimethylsilanyl-ethyl)-silanyl]-propyl]-dimethyl-amino)-butane-1-sulfonate (Figure 3). 2.45 g N,N-dimethyl aminopropyl pentamethyl carbodisilane 1 and 1.40 g1,4-butanesultone were dissolved in 10 ml dry THF. The mixture was heated to reflux overnight. After removing solvent, 2.94 g white solid was obtained.

Figure 3. Reaction Sequence for Preparation of Silane 3.

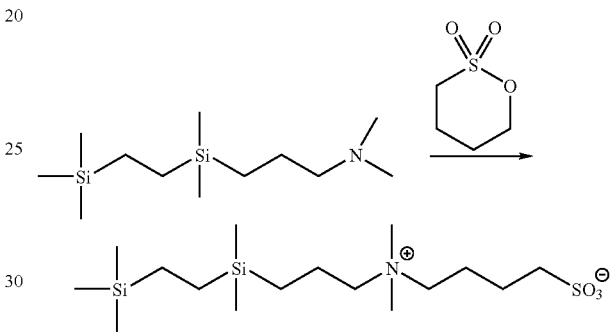

Preparation Example 4

3-([3-[Dimethyl-(2-trimethylsilanyl-ethyl)-silanyl]-propyl]-dimethyl-amino)-acetate (Figure 4). 2.45 g N,N-dimethyl aminopropyl pentamethyl carbodisilane 1 and 1.61 g sodium 2-bromoacetate were dissolved in 20 ml absolute ethanol. The suspension was heated to reflux overnight until all sodium 2-bromoacetate disappeared. After removing the solvent, the residue was washed with hexane and filtered 4.0 g white solid was obtained.

Figure 4. Reaction Sequence for Preparation of Silane 4.

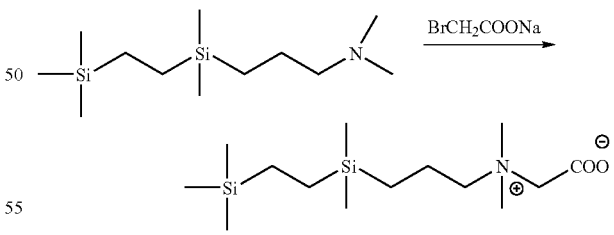

Preparation Example 5

3-([3-[Dimethyl-(2-trimethylsilanyl-ethyl)-silanyl]-propyl]-dimethyl-amino)-ethanol (Figure 5). 2.45 g N,N-dimethyl aminopropyl pentamethyl carbodisilane 1 and 1.37 g 2-bromoethanol were dissolved in 15 ml absolute ethanol. The mixture was heated to reflux for 16 hrs. After removing solvent, the residue was vacuumed at 100 degree C./0.1 mmHg for 2 hrs. 3.33 g white solid was obtained.

Figure 5. Reaction Sequence for Preparation of Silane 5.

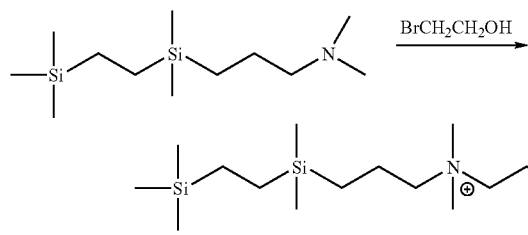

Preparation Example 6

3-([3-[Dimethyl-(2-trimethylsilanyl-ethyl)-silanyl]-propyl]-dimethyl-amino-ethoxy)-ethanol (Figure 6). 2.45 g N,N-dimethyl aminopropyl pentamethyl carbodisilane 1 and 1.37 g 2-chloroethoxy ethanol were dissolved in 10 ml absolute ethanol. The mixture was heated to reflux for 20 hrs. After removing solvent, the residue was vacuumed at 100 degree C./0.1 mmHg for 2 hrs. 2.58 g light yellow solid was obtained.
Figure 6. Reaction Sequence for Preparation of Silane 6 (n=2).

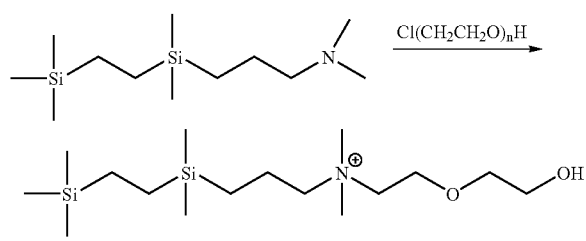

Preparation Example 7

3-([3-[Dimethyl-(2-trimethylsilanyl-ethyl)-silanyl]-propyl]-dimethyl-amino-ethoxy-ethoxy)-ethanol (Figure 7). 1.96 g N,N-dimethyl aminopropyl pentamethyl carbodisilane 1 and 1.26 g 2-(2-chloroethoxy)ethoxyethanol were dissolved in 10 ml absolute ethanol. The mixture was heated to reflux for 20 hrs. After removing solvent, the residue was vacuumed at 100 degree C./0.1 mmHg for 2 hrs. 1.38 g light yellow solid was obtained.
Figure 7. Reaction Sequence for Preparation of Silane 7 (n=3).

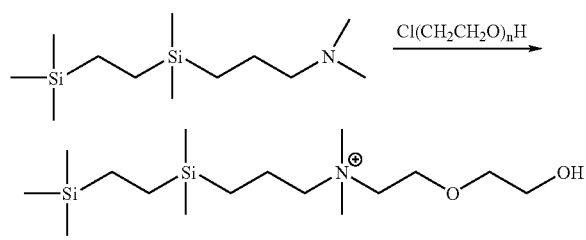

Preparation Example 8

2-{3-[Dimethyl-(2-trimethylsilanyl-ethyl)-silanyl]-propoxymethyl}-oxirane (Figure 8). Pentamethyl dicarbodisilane (12.8 g; 80 mMol) and Wilkinson's catalyst (30 ppm) were charged to a 100 mL RB 3 neck flask equipped with a magnetic stirrer, reflux condenser, and N$_2$ inlet. The mixture was stirred and heated to 90° C. 2-Allyloxymethyl-oxirane (10 g; 87.6 mMol) was placed in an addition funnel and added dropwise to the flask. The mixture was stirred and maintained at 90° C. for an additional 4 hours. The reaction progress was followed by NMR. Excess 2-allyloxymethyl-oxirane was removed by vacuum distillation.
Figure 8. Reaction Sequence for Preparation of Silylated Surfactant Intermediate 8.

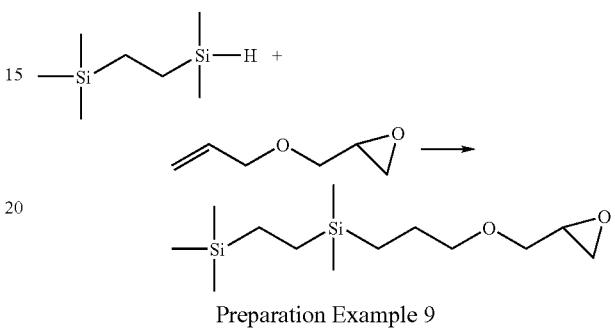

Preparation Example 9

1-{3-[Dimethyl-(2-trimethylsilanyl-ethyl)-silanyl]-propoxy}-3-[4-(2-hydroxy-ethyl)-piperazin-1-yl]-propan-2-ol (Figure 9). 2-piperazin-1-yl-ethanol (0.95 g; 7.28 mMol) and 20 mL of ethanol were charged to a 100 ml RB flask equipped with a magnetic stirrer. The mixture was stirred and heated to 70° C. 2-{3-[Dimethyl-(2-trimethylsilanyl-ethyl)-silanyl]-propoxymethyl}-oxirane 8 (2 g; 7.28 mMol) was placed in an addition funnel and added dropwise to the flask.

The mixture was stirred and maintained at 70° C. for additional 4 hours. After the reaction was complete, ethanol was stripped off on the rotovap. The mixture was distilled under vacuum.

Figure 9. Reaction Sequence for Preparation of Silane 9.

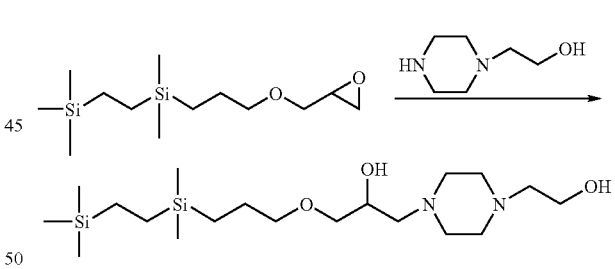

Preparation Example 10

1-{3-[Dimethyl-(2-trimethylsilanyl-ethyl)-silanyl]-propoxy}-3-[2-(2-hydroxy-ethoxy)-ethylamino]-propan-2-ol (Figure 10). 2-(2-amino-ethoxy)-ethanol (3.83 g; 36.4 mMol) and 40 mL of ethanol were charged to a 100 mL RB flask equipped with a magnetic stirrer. The mixture was stirred and heated to 70° C. 2-{3-[Dimethyl-(2-trimethylsilanyl-ethyl)-silanyl]-propoxymethyl}-oxirane 8 (2 g; 7.28 mMol) mixed with 10 g ethanol was placed in an addition funnel and added dropwise to the flask. The mixture was stirred and maintained at 70° C. for an additional 4 hours. Ethanol was stripped off on the rotovap. The mixture was distilled under vacuum to remove impurities and excess raw material.
Figure 10. Reaction Sequence for Preparation of Silane 10.

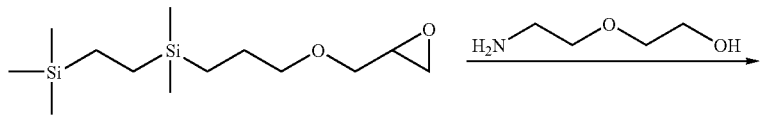

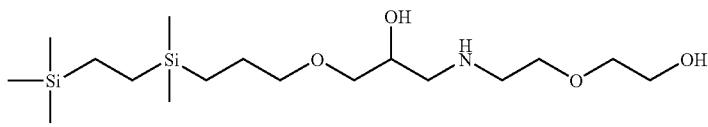

Preparation Example 11

1-{3-[Dimethyl-(2-trimethylsilanyl-ethyl)-silanyl]-propoxy}-3-[2-(2-hydroxy-ethoxy-ethoxy)-ethylamino]-propan-2-ol (Figure 11). 2-[2-(2-Amino-ethoxy)-ethoxy]-ethylamine (5.40 g; 36.4 mMol) and 40 mL of ethanol were charged to a 100 ml RB flask equipped with a magnetic stirrer. The mixture was stirred and heated to 70° C. 2-{3-[Dimethyl-(2-trimethylsilanyl-ethyl)-silanyl]-propoxymethyl}-oxirane 8 (2 g; 7.28 mMol) mixed with 10 g ethanol was placed in an addition funnel and added dropwise to the flask. The mixture was stirred and maintained at 70° C. for an additional 4 hours. Ethanol was stripped off on the rotovap. The mixture was distilled under vacuum to remove impurities and excess raw material.

Figure 11. Reaction Sequence for Preparation of Silane 11.

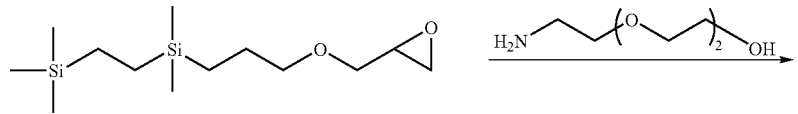

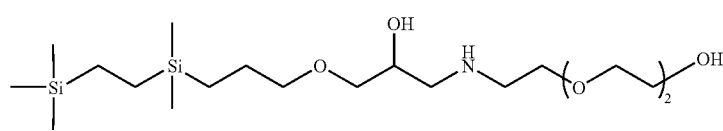

Preparation Example 12

1-{3-[Dimethyl-(2-trimethylsilanyl-ethyl)-silanyl]-propoxy}-3-morpholin-4-yl-propan-2-ol (Figure 12). Morpholine (0.634 g; 7.28 mMol) and 40 mL of ethanol were charged to a 100 mL RB flask equipped with a magnetic stirrer. The mixture was stirred and heated to 70° C. 2-{3-[Dimethyl-(2-trimethylsilanyl-ethyl)-silanyl]-propoxymethyl}-oxirane 8 (2 g; 7.28 mMol) mixed with 10 g ethanol was placed in an addition funnel and added dropwise to the flask. The mixture was stirred and maintained at 70° C. for an additional 4 hours. Ethanol was stripped off on the rotovap. The mixture was distilled under vacuum to remove impurities.

Figure 12. Reaction Sequence for Preparation of Silane 12.

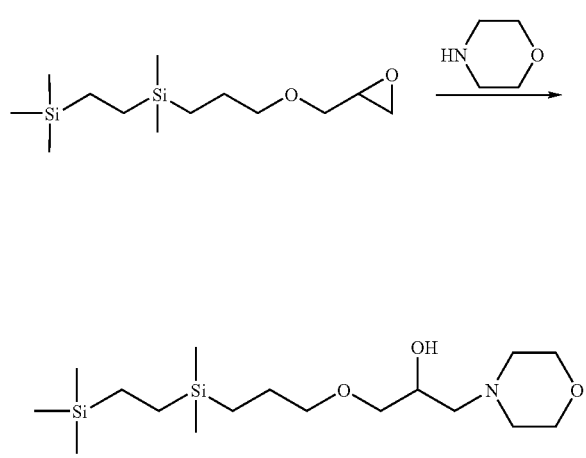

Preparation Example 13

1-{3-[Dimethyl-(2-trimethylsilanyl-ethyl)-silanyl]-propoxy}-3-piperazin-1-yl-propan-2-ol (Figure 13). Piperazine (3.14 g; 36.4 mMol) and 40 mL of ethanol were charged to a 100 mL RB flask equipped with a magnetic stirrer. The mixture was stirred and heated to 70° C. 2-{3-[Dimethyl-(2-trimethylsilanyl-ethyl)-silanyl]-propoxymethyl}-oxirane 8 (2 g; 7.28 mMol) mixed with 10 g ethanol was placed in an addition funnel and added dropwise to the flask. The mixture was stirred and maintained at 70° C. for an additional 4 hours. Ethanol was stripped off on the rotovap. The mixture was distilled under vacuum to remove impurities. Excess piperazine was removed by sublimation.

Figure 13. Reaction Sequence for Preparation of Silane 13.

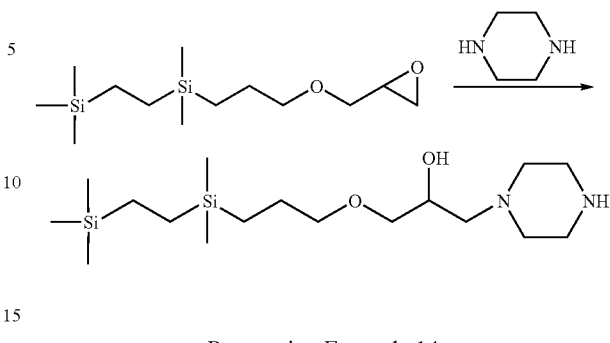

Preparation Example 14

1-[4-(2-Dimethylamino-ethyl)-piperazin-1-yl]-3-{3-[dimethyl-(2-trimethylsilanyl-ethyl)-silanyl]-propoxy}-propan-2-ol (Figure 14). Dimethyl-(2-piperazin-1-yl-ethyl)-amine (1.14 g; 7.28 mMol) and 40 mL of ethanol were charged to a 100 mL RB flask equipped with a magnetic stirrer. The mixture was stirred and heated to 70° C. 2-{3-[Dimethyl-(2-trimethylsilanyl-ethyl)-silanyl]-propoxymethyl}-oxirane 8 (2 g; 7.28 mMol) mixed with 10 g ethanol was placed in an addition funnel and added dropwise to the flask. The mixture was stirred and maintained at 70° C. for an additional 4 hours. Ethanol was stripped off on the rotovap. The mixture was distilled under vacuum to remove impurities.

Figure 14. Reaction Sequence for Preparation of Silane 14.

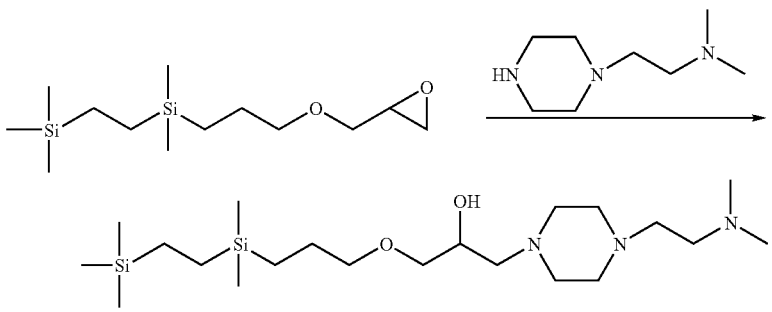

Preparation Example 15

1-{3-[Dimethyl-(2-trimethylsilanyl-ethyl)-silanyl]-propoxy}-3-(2-pyrrolidin-1-yl-ethylamino)-propan-2-ol (Figure 15). 2-Pyrrolidin-1-yl-ethylamine (4.16 g; 36.4 mMol) and 40 mL of ethanol were charged to a 100 mL RB flask equipped with a magnetic stirrer. The mixture was stirred and heated to 70° C. 2-{3-[Dimethyl-(2-trimethylsilanyl-ethyl)-silanyl]-propoxymethyl}-oxirane 8 (2 g; 7.28 mMol) mixed with 10 g ethanol was placed in an addition funnel and added dropwise to the flask. The mixture was stirred and maintained at 70° C. for an additional 4 hours. Ethanol was stripped off on the rotovap. The mixture was distilled under vacuum to remove impurities and excess 2-pyrrolidin-1-yl-ethylamine.

Figure 15. Reaction Sequence for Preparation of Silane 15.

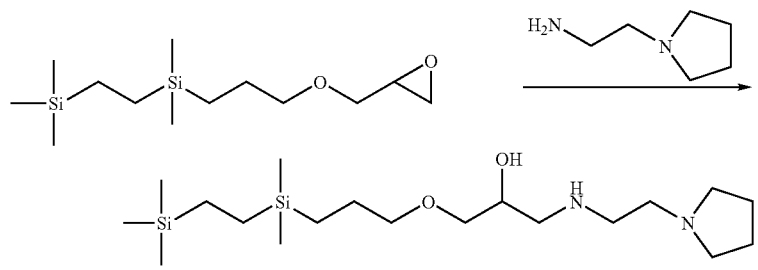

Preparation Example 16

1-{3-[Dimethyl-(2-trimethylsilanyl-ethyl)-silanyl]-propoxy}-3-(2-hydroxy-ethylamino)-propan-2-ol (Figure 16). 2-Amino-ethanol (2.22 g; 36.4 mMol) and 40 mL of ethanol were charged to a 100 mL R$^B$ flask equipped with a magnetic stirrer. The mixture was stirred and heated to 70° C. 2-{3-[Dimethyl-(2-trimethylsilanyl-ethyl)-silanyl]-propoxymethyl}-oxirane 8 (2 g; 7.28 mMol) mixed with 10 g ethanol was placed in an addition funnel and added dropwise to the flask. The mixture was stirred and maintained at 70° C. for an additional 4 hours. Ethanol was stripped off on the rotovap. The mixture was distilled under vacuum to remove impurities and excess 2-amino-ethanol.

Figure 16. Reaction Sequence for Preparation of Silane 16.

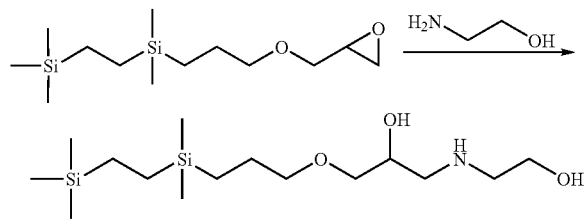

Preparation Example 17

1-{3-[Dimethyl-(2-trimethylsilanyl-ethyl)-silanyl]-propoxy}-3-(2-morpholin-4-yl-ethylamino)-propan-2-ol (Figure 17). 2-Morpholin-4-yl-ethylamine (4.74 g; 36.4 mMol) and 40 mL of ethanol were charged to a 100 mL RB flask equipped with a magnetic stirrer. The mixture was stirred and heated to 70° C. 2-{3-[Dimethyl-(2-trimethylsilanyl-ethyl)-silanyl]-propoxymethyl}-oxirane 8 (2 g; 7.28 mMol) mixed with 10 g ethanol was placed in an addition funnel and added dropwise to the flask. The mixture was stirred and maintained at 70° C. for an additional 4 hours. Ethanol was stripped off on the rotovap. The mixture was distilled under vacuum to remove impurities and excess 2-morpholin-4-yl-ethylamine.

Figure 17. Reaction Sequence for Preparation of Silane 17.

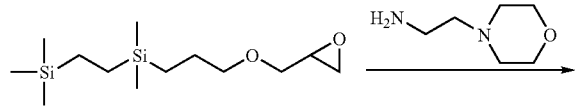

-continued

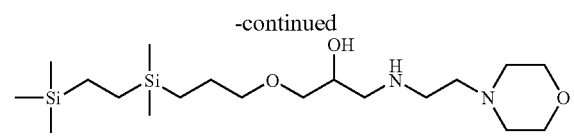

Preparation Example 18

1-{3-[Dimethyl-(2-trimethylsilanyl-ethyl)-silanyl]-propoxy}-3-[(tetrahydro-furan-2-ylmethyl)-amino]-propan-2-ol (Figure 18). C-(Tetrahydro-furan-2-yl)-methylamine (3.68 g; 36.4 mMol) and 40 mL of ethanol were charged to a 100 mL RB flask equipped with a magnetic stirrer. The mixture was stirred and heated to 70° C. 2-{3-[Dimethyl-(2-trimethylsilanyl-ethyl)-silanyl]-propoxymethyl}-oxirane 8 (2 g; 7.28 mMol) mixed with 10 g ethanol was placed in an addition funnel and added dropwise to the flask. The mixture was stirred and maintained at 70° C. for an additional 4 hours. Ethanol was stripped off on the rotovap. The mixture was distilled under vacuum to remove impurities and excess C-(Tetrahydro-furan-2-yl)-methylamine.

Figure 18. Reaction Sequence for Preparation of Silane 18.

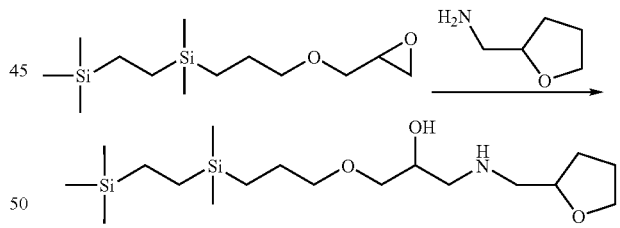

Preparation Example 19

1-Diethylamino-3-{3-[dimethyl-(2-trimethylsilanyl-ethyl)-silanyl]-propoxy}-propan-2-ol (Figure 19). Diethylamine (2.66 g, 36.4 mMol) and 40 mL of ethanol were charged to a 100 mL RB flask equipped with a magnetic stirrer. The mixture was stirred and heated to 60° C. 2-{3-[Dimethyl-(2-trimethylsilanyl-ethyl)-silanyl]-propoxymethyl}-oxirane 8 (2 g; 7.28 mMol) mixed with 10 g ethanol was placed in an addition funnel and added dropwise to the flask. The mixture was stirred and maintained at 60° C. for an additional 8 hours. Ethanol and diethyl amine were stripped off on the rotovap. The mixture was distilled under vacuum to remove impurities.

Figure 19. Reaction Sequence for Preparation of Silane 19.

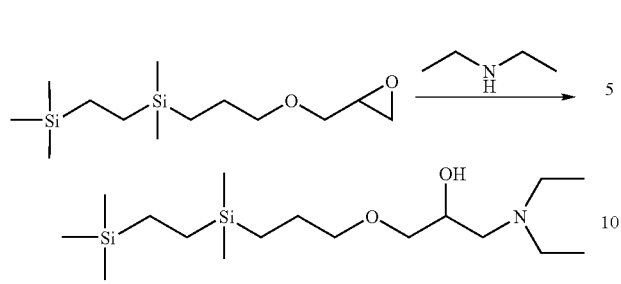

Preparation Example 20

1-Amino-3-{3-[dimethyl-(2-trimethylsilanyl-ethyl)-silanyl]-propoxy}-propan-2-ol (Figure 20). Aqueous ammonium hydroxide (25%; 10 g, 150 mMol) and 40 mL of ethanol were charged to a 100 mL RB flask equipped with a magnetic stirrer. The mixture was stirred and heated to 50° C. 2-{3-[Dimethyl-(2-trimethylsilanyl-ethyl)-silanyl]-propoxymethyl}-oxirane 8 (2 g; 7.28 mMol) mixed with 10 g ethanol was placed in an addition funnel and added dropwise to the flask. The mixture was stirred and maintained at 50° C. for an additional 8 hours. Ethanol and water were stripped off on the rotovap. The mixture was distilled under vacuum to remove impurities.

Figure 20. Reaction Sequence for Preparation of Silane 20.

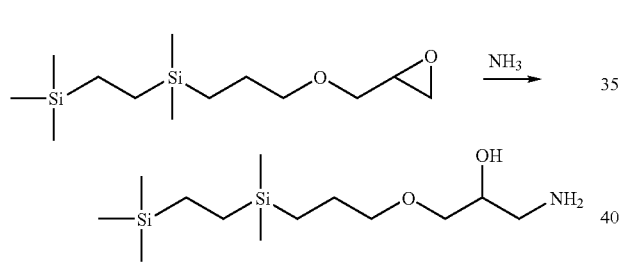

Preparation Example 21

1-Dimethylamino-3-{3-[dimethyl-(2-trimethylsilanyl-ethyl)-silanyl]-propoxy}-propan-2-ol (Figure 21). Aqueous dimethylamine (25%; 10 g, dimethyl amine 55 mMol) and 40 mL of ethanol were charged to a 100 mL RB flask equipped with a magnetic stirrer. The mixture was stirred and heated to 50° C. 2-{3-[Dimethyl-(2-trimethylsilanyl-ethyl)-silanyl]-propoxymethyl}-oxirane 8 (2 g; 7.28 mMol) mixed with 10 g ethanol was placed in an addition funnel and added dropwise to the flask. The mixture was stirred and maintained at 50° C. for an additional 8 hours. Ethanol, water and excess dimethyl amine were stripped off on the rotovap. The mixture was distilled under vacuum to remove impurities.

Figure 21. Reaction Sequence for Preparation of Silane 21.

-continued

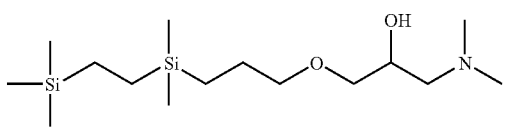

Preparation Example 22

1-{3-[Dimethyl-(2-trimethylsilanyl-ethyl)-silanyl]-propoxy}-3-isopropylamino-propan-2-ol (Figure 22). Isopropylamine (2.15 g, 36.4 mMol) and 40 mL of ethanol were charged to a 100 mL RB flask equipped with a magnetic stirrer. The mixture was stirred and heated to 60° C. 2-{3-[Dimethyl-(2-trimethylsilanyl-ethyl)-silanyl]-propoxymethyl}-oxirane 8 (2 g; 7.28 mMol) mixed with 10 g ethanol was placed in an addition funnel and added dropwise to the flask. The mixture was stirred and maintained at 60° C. for an additional 8 hours. Ethanol and isopropylamine were stripped off on the rotovap. The mixture was distilled under vacuum distillated to remove impurities.

Figure 22. Reaction Sequence for Preparation of Silane 22.

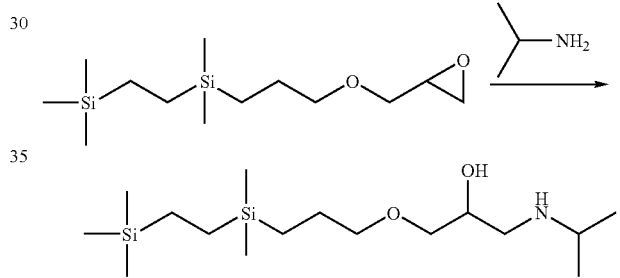

Preparation Example 23

1-Diisopropylamino-3-{3-[dimethyl-(2-trimethylsilanyl-ethyl)-silanyl]-propoxy}-propan-2-ol (Figure 23). Diisopropylamine (3.68 g, 36.4 mMol) and 40 mL of ethanol were charged to a 100 mL RB flask equipped with a magnetic stirrer. The mixture was stirred and heated to 60° C. 2-{3-[Dimethyl-(2-trimethylsilanyl-ethyl)-silanyl]-propoxymethyl}-oxirane 8 (2 g; 7.28 mMol) mixed with 10 g ethanol was placed in an addition funnel and added dropwise to the flask. The mixture was stirred and maintained at 60° C. for an additional 8 hours. Ethanol and diisopropylamine were stripped off on the rotovap. The mixture was distilled under vacuum to remove impurities.

Figure 23. Reaction Sequence for Preparation of Silane 23.

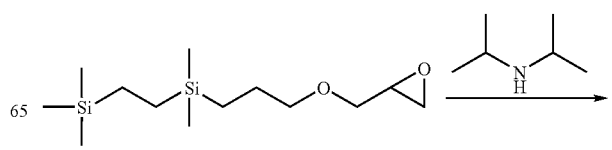

-continued

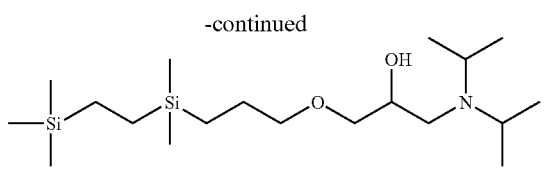

Preparation Example 24

6-[(3-{3-[Dimethyl-(2-trimethylsilanyl-ethyl)-silanyl]-propoxy}-2-hydroxy-propyl)-methyl-amino]-hexane-1,2,3,4,5-pentaol (Figure 24). N-methyl-D-glucamine (1.42 g; 7.28 mMol) and 40 mL of ethanol were charged to a 100 mL RB flask equipped with a magnetic stirrer. The mixture was stirred and heated to 70° C. 2-{3-[Dimethyl-(2-trimethylsilanyl-ethyl)-silanyl]-propoxymethyl}-oxirane 8 (2 g; 7.28 mMol) mixed with 10 g ethanol was placed in an addition funnel and added dropwise to the flask. The mixture was stirred and maintained at 70° C. for an additional 4 hours. Ethanol was stripped off on the rotovap. The mixture was distilled under vacuum to remove impurities.

Figure 24. Reaction Sequence for Preparation of Silane 24.

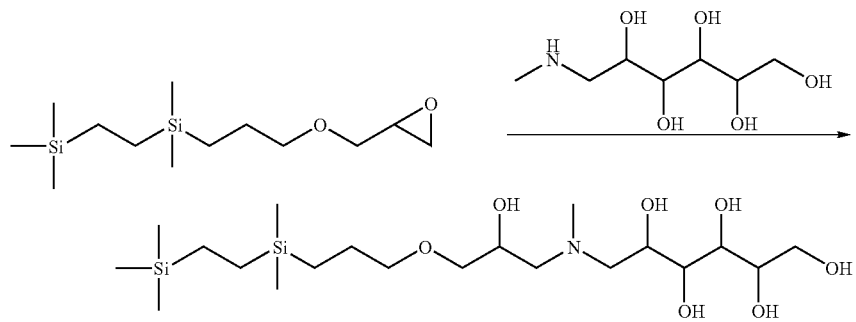

Comparative sample A is a trisiloxane ethoxylated surfactant containing 8.5 polyoxyethylene repeat units. This product is commercially available as Silwet® L-77 from GE Advanced Materials, Wilton, Conn.

Additionally, comparative sample OPE (Octylphenolethoxylate, containing 10 polyoxyethylene units) is a non-silicone organic surfactant. This product is available as Triton® X-100 from Dow Chemical Company, Midland, Mich.

Example 1

This example demonstrates the ability of the silane compositions of the present invention to reduce aqueous surface tension, thereby showing utility as surfactants. Surface tension was measured using pendant drop analysis. Solutions of the various components were prepared at 0.1 wt % in water (deionized), 2M $NH_4Cl$ solution, or 10 wt. % NaCl solution.

Table 1 shows that solutions of these unique compositions provide a significant reduction in surface tension relative to the conventional surfactant.

The compositions of the present invention also provide spreading properties similar to the comparative trisiloxane surfactant A. Additionally, silanes of the present invention provide improved spreading relative to the conventional organic surfactant product OPE.

Spreading was determined by applying a 10 μL droplet, of surfactant solution to polystyrene Petri dishes (Fisher Scientific) and measuring the spread diameter (mm) after 30 seconds, at a relative humidity between 50 and 70% (at 22 to 25° C.). The solution was applied with an automatic pipette to provide droplets of reproducible volume. Deionized water that was further purified with a Millipore filtration system was used to prepare the surfactant solutions.

TABLE 1

Surface Tension and Spreading Properties

| | Surface | Spread Diameter (mm) 0.1 Weight % Surfactant | | |
|---|---|---|---|---|
| I.D. | Tension (mN/m) | DI Water | 2M $NH_4Cl$ | 10% NaCl |
| 2 | 31.4 | 5 | nd | 17 |
| 4 | 23.6 | 4 | nd | 40 |
| 5 | 45.0 | 4 | nd | 33 |
| 6 | 27.9 | 4 | nd | 10 |
| 7 | 27.4 | 4 | nd | nd |
| 9 | 22.6 | 44 | 33 | nd |
| 10 | 22.0 | 45 | 42 | nd |

TABLE 1-continued

Surface Tension and Spreading Properties

| | Surface | Spread Diameter (mm) 0.1 Weight % Surfactant | | |
|---|---|---|---|---|
| I.D. | Tension (mN/m) | DI Water | 2M $NH_4Cl$ | 10% NaCl |
| 11 | 22.3 | 34 | 8 | nd |
| 12 | 23.5 | 7 | 40 | nd |
| 13 | 22.3 | 9 | 30 | nd |
| 14 | 23.1 | 29 | 18 | nd |
| 15 | 22.8 | 14 | 16 | nd |
| 16 | 22.6 | 14 | 35 | nd |
| 17 | 22.2 | 36 | 36 | nd |
| 18 | 23.8 | 8 | 36 | nd |
| 19 | 22.9 | 4 | 40 | nd |
| 20 | 22.7 | 6 | 45 | nd |
| 21 | 21.9 | 6 | 50 | nd |
| 22 | 20.7 | 5 | 37 | nd |
| 23 | Insol | 4 | 50 | nd |
| 24 | 22.7 | 11 | 30 | nd |
| A | 20.9 | 53 | nd | nd |
| OPE | 31.8 | 9 | nd | nd |

Example 2

Unlike traditional siloxane based surfactants, which are subject to rapid hydrolysis under acidic and basic conditions (≦pH 5 and ≧pH 9), the silanes of the present invention provide increased resistance to hydrolysis relative to traditional trisiloxane alkoxylates (Comparative Example A). An artifact of hydrolysis is observed as a reduction in spreading properties over time. Therefore, solutions of the silanes of the present invention, as well as comparative surfactants, were prepared at desired use levels and pH. Spreading was determined as a function of time to illustrate resistance to hydrolysis.

Table 2 is an illustrative example of a traditional organo-modified trisiloxane ethoxylate surfactant, which exhibits decreased spreading performance with time as a function of hydrolytic decomposition over a pH range from pH 3 to pH 10. Here a 0.4 wt % solution of sample A was prepared at pH 3, 4, 5 and 10. Spreading was determined by applying a 10 μL droplet of surfactant solution to polyacetate film (USI, "Crystal Clear Write on Film") and measuring the spread diameter (mm) after 30 seconds, at a relative humidity between 50 and 70% (at 22 to 25° C.). The solution was applied with an automatic pipette to provide droplets of reproducible volume. Deionized water that was further purified with a Millipore filtration system was used to prepare the surfactant solutions.

TABLE 2

Effect of pH on Spreading Properties Vs. Time

| | | Spread Diameter (mm) | | | |
|---|---|---|---|---|---|
| Time | Product | pH 3 | pH 4 | pH 5 | pH 10 |
| 0 h | A | 34 | 28 | 29 | 27 |
| 1 h | A | 39 | 37 | 27 | 33 |
| 2 h | A | 36 | 30 | 33 | 33 |
| 4 h | A | 41 | 28 | 28 | 29 |
| 6 h | A | 16 | 27 | 27 | 28 |
| 8 h | A | 12 | 31 | 29 | 27 |
| 24 h | A | 12 | 32 | 25 | 25 |
| 48 h | A | 10 | 41 | 25 | 33 |
| 5 days | A | 7 | 30 | 26 | 36 |
| 7 days | A | 6 | 17 | 28 | 25 |
| 14 days | A | 7 | 7 | 37 | 15 |

Example 3

Table 3 is an illustrative example of an silane of the present invention, where sample 4, a superspreader, has improved resistance to hydrolysis, over a pH range from pH 4 to pH 11 relative to a traditional trisiloxane ethoxylate surfactant (Product A). As mentioned above, resistance to hydrolysis was observed by monitoring the spreading properties over time. Here a 0.1 wt % solution of surfactant was prepared in distilled water containing 10 wt. % NaCl at pH 4, 5, 9 and 11. Spreading was determined by applying a 10 μL droplet, of surfactant solution to polystyrene Petri dishes (Fisher Scientific) and measuring the spread diameter (mm) after 30 seconds, at a relative humidity between 50 and 70% (at 22 to 25° C.). The solution was applied with an automatic pipette to provide droplets of reproducible volume.

TABLE 3

Effect of pH on Spreading Properties Vs. Time

| | | Spread Diameter (mm) | | | |
|---|---|---|---|---|---|
| Time | Product | pH 4 | pH 5 | pH 9 | pH 11 |
| 0 h | 4 | 43 | 44 | 43 | 44 |
| 24 h | 4 | 43 | 44 | 42 | 42 |
| 192 h | 4 | 46 | 45 | 42 | 42 |
| 2 weeks | 4 | 46 | 45 | 41 | 41 |
| 1 month | 4 | 46 | 45 | 40 | 43 |
| 2 months | 4 | 45 | 46 | 42 | 41 |

Example 4

Table 4 is an illustrative example of an silane of the present invention, where sample 5, a superspreader, has improved resistance to hydrolysis, over a pH range from pH 4 to pH 11 relative to a traditional trisiloxane ethoxylate surfactant (Product A). As mentioned above, resistance to hydrolysis was observed by monitoring the spreading properties over time. Here a 0.1 wt % solution of surfactant was prepared in distilled water containing 10 wt. % NaCl at pH 4, 5, 9 and 11. Spreading was determined by applying a 10 μL droplet, of surfactant solution to polystyrene Petri dishes (Fisher Scientific) and measuring the spread diameter (mm) after 30 seconds, at a relative humidity between 50 and 70% (at 22 to 25° C.). The solution was applied with an automatic pipette to provide droplets of reproducible volume.

TABLE 4

Effect of pH on Spreading Properties Vs. Time

| | | Spread Diameter (mm) | | | |
|---|---|---|---|---|---|
| Time | Product | pH 4 | pH 5 | pH 9 | pH 11 |
| 0 h | 5 | 18 | 18 | 20 | 21 |
| 24 h | 5 | 19 | 18 | 22 | 25 |
| 192 h | 5 | 19 | 18 | 21 | 24 |
| 2 weeks | 5 | 22 | 20 | 24 | 26 |
| 1 month | 5 | 19 | 20 | 24 | 24 |
| 2 months | 5 | 22 | 23 | 24 | 26 |

The foregoing examples are merely illustrative of the invention, serving to illustrate only some of the features of the present invention. The appended claims are intended to claim the invention as broadly as it has been conceived and the examples herein presented are illustrative of selected embodiments from a manifold of all possible embodiments. Accordingly it is the Applicants intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "onsisting essentially of" and "onsisting of." Where necessary, ranges have been supplied, those ranges are inclusive of all sub-ranges there between. Such ranges may be viewed as a Markush group or groups consisting of differing pairwise numerical limitations which group or groups is or are fully defined by its lower and upper bounds, increasing in a regular fashion numerically from lower bounds to upper bounds. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims. All United States patents (and patent applications) referenced herein are herewith and hereby specifically incorporated by reference in their entirety as though set forth in full.

Having described the invention we claim:

1. A composition comprising a silane having the formula:

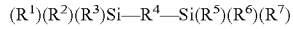

$(R^1)(R^2)(R^3)Si—R^4—Si(R^5)(R^6)(R^7)$ wherein $R^1$, $R^2$, $R^3$, $R^5$ and $R^6$ are each methyl;

$R^4$ is a hydrocarbon group of 1 to 3 carbons;

$R^7$ is selected from the group consisting of $R^9—R^C$ and $R^{10}—R^Z$;

$R^9$ is a monovalent radical selected from the group consisting of $R^{16}(O)_w(R^{17})_x—$ and $R^{18}O(C_2H_4O)_d(C_3H_6O)_e(C_6H_8O)_f$ $CH_2CH(OH)CH_2$;

where $R^{16}$ and $R^{17}$ are each independently selected from the group consisting of a divalent hydrocarbon group of 1 to 4 carbon atoms; $R^{18}$ is a divalent hydrocarbon group of 2 to 4 carbon atoms; subscripts w and x are 1;

the subscripts d, e and f are zero or positive and satisfy the following relationships:

$1 \leq d+e+f \leq 10$ with $d \geq 1$;

$R^C$ is selected from the group consisting of $N(R^{19})(R^{20})$,

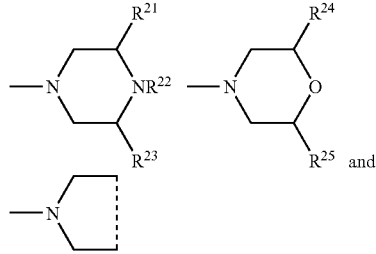

where $R^{19}$ and $R^{20}$ are independently selected from the group consisting of H, a branched or linear monovalent hydrocarbon radical of 1 to 4 carbons, $R^{26}N(R^{29})(R^{30})$, and $—R^{27}O(C_2H_4O)_g(C_3H_6O)_h(C_4H_8O)_iR^{28}$;

the subscripts g, h and i are zero or positive and satisfy the following relationships:

$1 \leq g+h+i \leq 10$ with $g \geq 1$;

$R^{21}$, $R^{23}$, $R^{24}$, $R^{25}$ are each independently selected from the group consisting of H and branched or linear monovalent hydrocarbon radicals of 1 to 4 carbons;

$R^{22}$ is a monovalent radical selected from the group consisting of H, branched or linear monovalent hydrocarbon radical of 1 to 4 carbons, and $—R^{31}O(C_2H_4O)_j(C_3H_6O)_k(C_4H_8O)_lR^{32}$;

the subscripts j, k and l are zero or positive and satisfy the following relationships:

$1 \leq j+k+l \leq 10$ with $j \geq 1$;

$R^{26}$ is a divalent hydrocarbon radical of 1 to 6 carbons, or $R^{33}O(C_2H_4O)_m(C_3H_6O)_n(C_4H_8O)_oR^{34}$;

the subscripts m, n and o are zero or positive and satisfy the following relationships:

$1 \leq m+n+o \leq 10$ with $m \geq 1$;

$R^{29}$ and $R^{30}$ are independently selected from the group consisting of H, branched monovalent hydrocarbon radical of 1 to 4 carbons, and linear monovalent hydrocarbon radical of 1 to 4 carbons;

$R^{27}$, $R^{31}$ and $R^{33}$ are independently selected from the group consisting of a divalent hydrocarbon group of 2 to 4 carbon atoms;

$R^{28}$ is a monovalent radical selected from the group consisting of H, a monovalent hydrocarbon radical of 1 to 6 carbons and $N(R^{40})(R^{41})$;

$R^{32}$ and $R^{34}$ are independently selected from the group consisting of H, a branched or linear monovalent hydrocarbon radical of 1 to 4 carbons, and $R^{37}N(R^{38})(R^{39})$;

where $R^{37}$ is a divalent hydrocarbon radical of 1 to 6 carbons;

$R^{35}$, $R^{36}$, $R^{38}$ and $R^{39}$ are independently selected from the group consisting of H and branched or linear monovalent hydrocarbon radicals of 1 to 4 carbons;

$R^{10}$ is a monovalent radical selected from the group consisting of $R^{40}(O)_y(R^{41})_z—$ and $R^{42}O(C_2H_4O)_p(C_3H_6O)_q(C_6H_8O)_rCH_2CH(OH)CH_2—$;

where $R^{40}$ and $R^{41}$ are each independently selected from the group consisting of a divalent hydrocarbon group of 1 to 4 carbon atoms;

$R^{42}$ is a divalent hydrocarbon group of 2 to 4 carbon atoms;

the subscripts y and z are 1;

the subscripts p, q and r are zero or positive and satisfy the following relationships:

$1 \leq p+q+r \leq 10$ with $p \geq 1$;

$R^Z$ is $—N—(R^{43})(R^{44})_\alpha R^{45}SO_3(M^K)_\beta$, $—N—(R^{46})(R^{47})_\gamma R^{48}COO(M^K)_\delta$, $—N^+—(R^{49})(R^{50})R^{51}OP(=O)(A)(B)$ or, $(—C(=O)N(R^{52})R^{53}N—(R^{54})(R^{55}))^+—(R^{56}(=O)(A)(B)(X^-)_\epsilon$;

where $R^{43}$, $R^{44}$, $R^{46}$, $R^{47}$, $R^{49}$, $R^{50}$, $R^{52}$, $R^{54}$ and $R^{55}$ are independently selected from the group consisting of H, branched monovalent hydrocarbon radical of 1 to 4 carbons, linear monovalent hydrocarbon radical of 1 to 4 carbons and an alkanolamine group having alkyl groups of 2 to 4 carbons; and $R^{45}$ is a divalent group of 3 to 4 carbons;

$M^K$ is a cation selected from the group consisting of $Na^+$, $K^+$, $Ca^{2+}$, $NH^{4+}$, and $Li^+$, monovalent ammonium ions derived from mono-, di- and trialkylamines comprising alkyl groups of 2 to 4 carbons, and mono-, di- and trialkanolamines comprising alkyl groups of 2 to 4 carbons;

subscripts $\alpha$, $\beta$, $\gamma$ and $\delta$ are zero or 1 subject to the following relationships:

$\alpha+\beta=1$ and $\gamma+\delta=1$;

$R^{48}$ and $R^{51}$ are independently a divalent group of 1 to 4 carbons;

$R^{53}$ and $R^{56}$ are each independently a divalent group of 2 to 4 carbons;

A and B are selected from $O—$ and $OM^K$; X is an anion selected from the group consisting of Cl, Br, and I; and the subscript $\epsilon$ is 0, 1 or 2.

2. The composition of claim 1 where $R^7$ is $R^9$-$R^C$.

3. The composition of claim 1 where $R^C$ is $N(R^{19})(R^{20})$.

4. The composition of claim 1 where $R^7$ is $R^{10}$-$R^Z$.

5. The composition of claim 1 where $R^Z$ is $—N—(R^{43})(R^{44})_\alpha R^{45}SO_3(M^K)_\beta$.

6. The composition of claim 1 where $R^Z$ is $—N—(R^{46})(R^{47})_\gamma R^{48}COO(M^K)_\delta$.

* * * * *